United States Patent
Kawana

(10) Patent No.: US 9,582,909 B2
(45) Date of Patent: Feb. 28, 2017

(54) CHROMATOGRAPH MASS SPECTROMETRY DATA PROCESSING DEVICE

(71) Applicant: SHIMADZU CORPORATION, Kyoto-shi, Kyoto (JP)

(72) Inventor: Shuichi Kawana, Kyoto (JP)

(73) Assignee: SHIMADZU CORPORATION, Kyoto (JP)

(*) Notice: Subject to any disclaimer, the term of this patent is extended or adjusted under 35 U.S.C. 154(b) by 37 days.

(21) Appl. No.: 13/678,088

(22) Filed: Nov. 15, 2012

(65) Prior Publication Data

US 2014/0132607 A1    May 15, 2014

(51) Int. Cl.
  *G01N 30/72*  (2006.01)
  *G06T 11/20*  (2006.01)
  *G01N 30/86*  (2006.01)

(52) U.S. Cl.
  CPC ......... *G06T 11/206* (2013.01); *G01N 30/8675* (2013.01); *G01N 30/72* (2013.01); *G01N 30/8624* (2013.01)

(58) Field of Classification Search
  CPC ........ G06T 11/206; G06T 15/00; G06F 19/70; G06F 19/708; G06F 19/703; G06F 19/707; G06F 15/00; G06F 17/00; G06F 17/30294; G06F 17/30566; G06K 9/00523; G06K 9/00496; G06K 9/00536; G06K 9/0053
  See application file for complete search history.

(56) References Cited

U.S. PATENT DOCUMENTS

2001/0007349 A1*  7/2001  Nagai .............................. 250/281
2007/0147685 A1*  6/2007  Ericson .......................... 382/225
(Continued)

FOREIGN PATENT DOCUMENTS

JP    S59-164954 A    9/1984
JP    H3-105248 A    5/1991
(Continued)

OTHER PUBLICATIONS

NIST, Engineering Statistics Handbook, 6.3.1. What are Control Charts? website URL http://www.itl.nist.gov/div898/handbook/pmc/section3/pmc31.htm with the URL for wayback machine http://web.archive.org/web/20110303084128/http://www.itl.nist.gov/div898/handbook/pmc/section3/pmc31.htm.*

(Continued)

*Primary Examiner* — Jacinta M Crawford
*Assistant Examiner* — Phuc Doan
(74) *Attorney, Agent, or Firm* — Sughrue Mion, PLLC

(57) ABSTRACT

A measurement EIC for quantitative ions and a measurement EIC for ions to be confirmed in the vicinity of the retention time of a target compound are displayed in an overlapping manner in a chromatogram display area. In addition, a standard center line corresponding to a standard value of the confirmation ion ratio, which expresses the ratio of the intensity of the confirmation ions to the intensity of the quantitative ions in the target compound and an upper limit line and a lower limit line demonstrating the permissible range of the intensity of the confirmation ions are displayed in an overlapping manner on the EIC. An analyst determines whether a peak used for identification originates from the target compound by determining whether the top of an EIC peak of the confirmation ions falls between the upper limit line and the lower limit line.

6 Claims, 3 Drawing Sheets

(56) References Cited

U.S. PATENT DOCUMENTS

2010/0134532 A1\* 6/2010 Choi et al. ............... 345/690
2010/0304254 A1\* 12/2010 Crumm et al. ........... 429/432

FOREIGN PATENT DOCUMENTS

| JP | 2006-189279 A | 7/2006 |
|---|---|---|
| JP | 2007-147464 A | 6/2007 |
| WO | WO2012075046 | \* 11/2011 |

OTHER PUBLICATIONS

Wiki, Isotopic labeling, URL: https://en.wikipedia.org/wiki/Isotopic_labeling.\*
Johnson, Quantification of saxitoxin and neosaxitoxin in human urine utilizing isotope dilution tandem mass spectrometry, Journal of Analytical Toxicology, vol. 33, Jan./Feb. 2009, pp. 8-14.*

Japanese Office Action dated May 21, 2013 with partial English translation.

* cited by examiner

CHROMATOGRAPH MASS SPECTROMETRY DATA PROCESSING DEVICE

TECHNICAL FIELD

The present invention relates to a data processing device for processing data collected by a chromatograph mass spectrometer using a mass spectrometer (MS) as a detector for a gas chromatograph (GC) or a liquid chromatograph (LC); more specifically, the present invention relates to data processing technology for a man-machine interface for screen display processing, operation input processing, or the like in a chromatograph mass spectrometer.

BACKGROUND ART

In GC/MS analysis, various components contained in a test sample are passed through a column and separated over time, and the ions generated from each of the separated components are separated according to their mass-charge ratios (m/z) by a mass spectrograph such as a quadrupole mass filter and detected with a detector. When identifying unknown compounds contained in a sample, scan measurements of prescribed mass ranges (m/z ranges) are ordinarily executed repeatedly in MS, and a mass spectrum is created for each of the scan measurements. A graph in which the intensity determined by adding all of the ion intensities in each mass spectrum is plotted over time is a total ion current chromatogram (TIC), and a graph in which attention is focused on ions having certain mass-charge ratios and the intensities of these ions are plotted over time is an extracted ion chromatogram (EIC).

When assaying a compound contained in a sample by GC/MS analysis or LC/MS analysis, the ions characterizing the compound are typically determined to be quantitative ions (also called target ions), and quantitative values—that is, the component content or concentration—are calculated from the chromatogram peaks appearing in the vicinity of the retention time of the target compound in an EIC of the quantitative ions obtained by means of actual measurements. Ions corresponding to a peak for which the signal intensity is highest in a typical mass spectrum of the compound are ordinarily selected as quantitative ions.

Although the quantitative ions described above are ions which characterize each compound, various contaminants may be included in an actual sample, and components may overlap due to insufficient component separation in the previous stage of GC or LC as a result of inappropriate analytical conditions. In such cases, it is sometimes difficult to confirm from chromatogram peaks of quantitative ions alone whether the peaks indeed originate from the target compound. In such cases, ions having a different mass-charge ratio characterizing the compound are selected as confirmation ions separately from the quantitative ions, and it is confirmed—that is, identified—that the chromatogram peaks of the quantitative ions originate from the target compound using the relative ratio (hereafter called the "confirmation ion ratio") of the signal intensity of the confirmation ion peaks and the signal intensity of the quantitative ion peaks in the mass spectrum. In addition, confirmation ions of one type are often insufficient to accurately confirm the quantitative ion peaks of a compound, and it is common for a plurality of types of confirmation ions to be used for a single compound (see Patent Document 1).

In a conventional device, a confirmation ion ratio found from data obtained by performing mass spectrometry on a standard sample of a target compound is stored in advance in a storage part as an ideal ratio, and an analyst is able to determine whether the confirmation ion ratio of an identified compound is appropriate by comparing the numerical value of the confirmation ion ratio found from data obtained by analyzing the actual sample and the ideal ratio described above. However, such a determination by numerical values is not very efficient and is prone to misjudgment. Moreover, in order for the analyst to determine whether the identification of a compound is appropriate, it is also necessary to visually confirm the shapes and heights of peaks in the EIC, but it is difficult for the analyst to determine whether a peak height is appropriate based on the confirmation ion ratio by simply examining the EIC.

In particular, in the case of multi-component analysis, it is necessary for the analyst to visually confirm whether peaks in the EIC are appropriate based on the confirmation ion ratio one by one for an enormous number of compounds ranging from several tens to several hundreds of compounds. Therefore, in order to increase the throughput of such an operation, the analyst is required to assess the appropriateness of each compound in a short amount of time, but such an assessment is difficult to make in a short amount of time with the conventional method described above, and there is also a high probability of causing misjudgment and oversight.

Patent Document 1—Japanese Unexamined Patent Application Publication 2006-189279

SUMMARY OF THE INVENTION

The present invention was conceived in light of the problems described above, and its purpose is to provide a chromatograph mass spectrometry data processing device capable of improving operating efficiency by simplifying the operations performed by an analyst and reducing operational mistakes when performing component identification or quantitative analysis by analyzing data collected by means of chromatograph mass spectrometry.

The present invention, which was conceived in order to solve the problems described above, is a chromatograph mass spectrometry data processing device for creating extracted ion chromatograms (EIC) with respect to specific mass-charge ratios based on data repeatedly collected over time by chromatograph mass spectrometry and displaying the chromatograms on a display screen, the device being provided with:

a) a standard information storage means for storing the retention times, the mass-charge ratios of quantitative ions and confirmation ions, and standard values of a confirmation ion ratio expressing the ratio of the intensity of confirmation ions to quantitative ions for various components;

b) a chromatogram display processing means for creating extracted ion chromatograms of the quantitative ions and confirmation ions of the target components based on actual measurement data of the target components designated to be confirmed among the various components stored in the standard information storage means and displaying the chromatograms in an overlapping manner within the boundaries of the same graph; and c) an additional display processing means for obtaining standard values of the confirmation ion ratios of the target components corresponding to the confirmation ions for which extracted ion chromatograms are displayed by the chromatogram display processing means from the standard information storage means and graphically displaying information showing the standard values on the displayed extracted ion chromatograms.

The chromatograph mass spectrometry data processing device of the present invention can be realized by executing a dedicated computer program for realizing functions corresponding to each of the means described above on a general-purpose computer comprising a display part, an operation part (keyboard, pointing device, or the like), and the like.

In addition, in the chromatograph mass spectrometry data processing device of the present invention information showing the standard values of confirmation ion ratios of target components should typically be shown as a horizontal line in an overlapping manner in the EIC of quantitative ions and confirmation ions. If there are a plurality of confirmation ions for a single target component, the EICs of the plurality of confirmation ions should be displayed in an overlapping manner with different line colors, for example, and the standard values of the confirmation ion ratios corresponding to each of the confirmation ions should also be similarly displayed in an overlapping manner with different line colors.

Moreover, in the chromatograph mass spectrometry data processing device of the present invention, an analyst or the like should select components to be identified or components for which content is to be confirmed from among the various components stored in the standard information storage means in advance and create a table in which these components are registered so that the analyst can select target components by designating arbitrary components from the table.

If the selected target components are components which have been automatically identified using the retention time, the similarity of mass spectrum patterns, the confirmation ion ratio, or the like, the chromatogram display processing means should display an EIC in which the vicinities of peaks identified in the EIC of quantitative ions are magnified. On the other hand, if the selected target components are components which have not been automatically identified, the peaks closest to the retention times of the target components in the EIC of quantitative ions should be considered to be chromatogram peaks corresponding to those components, and an EIC in which the vicinities of the peaks are magnified should be displayed.

With the chromatograph mass spectrometry data processing device of the present invention, it becomes possible to confirm the peak waveforms originating from target components appearing in an EIC of the confirmation ions of the target components and the ideal intensity ratios of the confirmation ions at a glance within the boundaries of the same graph. Accordingly, the analyst can intuitively and quickly determine whether the peak heights of confirmation ions is approximately the same as the standard value of the confirmation ion ratio. In addition, since the waveform shapes of the peaks of quantitative ions or confirmation ions of target components demonstrated by actual measurements can also be confirmed, it is also possible to simultaneously determine the deformation of peak waveforms caused by the overlapping of non-target components such as contaminants. As a result, when performing operations such as the confirmation of whether target components are present in a sample or the identification of components contained in a sample, the confirmation operation performed visually by the analyst is simplified, which improves the operating efficiency, and the reliability of the results is also improved due to the reduction of operating mistakes.

Further, in the chromatograph mass spectrometry data processing device of the present invention, it is preferable for the additional display processing means to be configured so as to graphically display information showing a permissible intensity range around the standard values of the confirmation ion ratios on the displayed extracted ion chromatograms. With such a configuration, it is possible to even more simply determine whether the peak heights of confirmation ions fall within a permissible range around the standard values of the confirmation ion ratios.

DETAILED DESCRIPTION OF THE EXEMPLARY EMBODIMENTS

Figure 1:
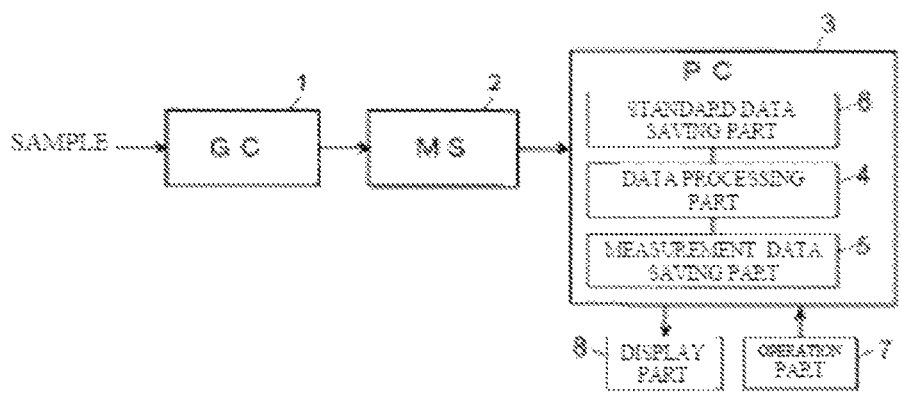
FIG. 1 is a schematic block diagram of an embodiment of a GC-MS system containing the data processing device of the present invention.

A GC-MS system containing the chromatograph mass spectrometry data processing device of the present invention will be described below with reference to the attached drawings. FIG. 1 is a schematic block diagram of an embodiment of a GC-MS system according to this embodiment.

This system is provided with a gas chromatograph (GC) 1 for separating components contained in a sample over time, a mass spectrometer (MS) 2 for separating and detecting each of the separated components according to the mass-charge ratio (m/z), and a personal computer (PC) 3 for processing data obtained by the MS 2. Dedicated data processing software is installed in the PC 3, the functions of a data processing part 4, a measurement data saving part 5, a standard data saving part 6, and the like shown in the drawing are realized by executing this software with the PC 3. In addition, an operation part 7, which is a pointing device such as a keyboard or a mouse, and a display part 8 are connected to the PC 3.

Figure 2:
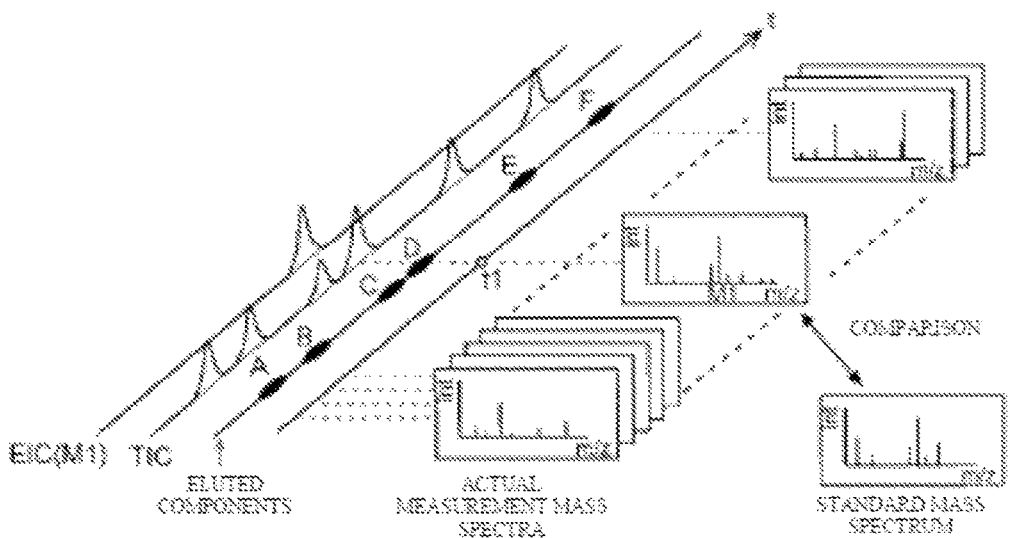
FIG. 2 is a schematic diagram showing the data collection operation and the obtained data in the GC-MS system of this embodiment.

FIG. 2 is a schematic diagram for explaining data collected at the time of analysis in the GC-MS system described above. The data collection operation of the GC-MS system will be explained briefly using FIGS. 1 and 2.

When a sample is introduced into the GC 1, the components contained in the sample are separated and eluted while they are passed through a column (not shown). In the example shown in FIG. 2, six types of components A, B, C, D, E, and F are eluted at different times. In the MS 2, scan measurements involving mass scans of prescribed mass ranges are repeated at regular time intervals. One scanning measurement (mass scan) yields data (mass spectrum data) constituting one actual measurement mass spectrum such as that shown in FIG. 2. Accordingly, the actual measurement mass spectrums are obtained at the predetermined time intervals by repeating the scan measurements at the predetermined time intervals. All of the ion intensities contained in a single actual measurement mass spectrum are added, and a plot of the results in the time direction is a TIC, whereas a graph in which attention is focused on only specific mass-charge ratios and the ion intensities of the mass-charge ratios are plotted in the time direction is an EIC. In the example of FIG. 2, an EIC for m/z=M1 corresponding to peaks appearing in the actual measurement mass spectrum at time t1 is shown.

In the GC-MS system of this embodiment, mass spectrum data is repeatedly collected as described above from the point when the sample is introduced into the GC 1 (or a point delayed by a prescribed amount of time thereafter) until a point delayed by an appropriate amount of time after the components in the sample are completely eluted, and this is consolidated into a single data file and stored in the measurement data saving part 5. The measurement data stored in the measurement data saving part 5 is read into the data processing part 4 when designated by the analyst and is used in reanalysis for the purpose of component identification or assay.

On the other hand, the retention times of various compounds, the mass-charge ratio of a single quantitative ion, the mass-charge ratio of one or a plurality of confirmation ions, standard values of the confirmation ion ratios of each of the confirmation ions ((confirmation ion intensity/quantitative ion intensity)×100[%]), standard mass spectra, and the like are registered in advance in the standard data saving part 6. As data to be stored in this standard data saving part 6, the data listed in a typically provided database such as the NIST, Wiley, or Drug database may be used directly, or a part of the database may be extracted and used. In addition, data created independently by a device manufacturer and provided to the user or data obtained based on measurements of standard substances taken by the user himself may also be used.

Figure 3:
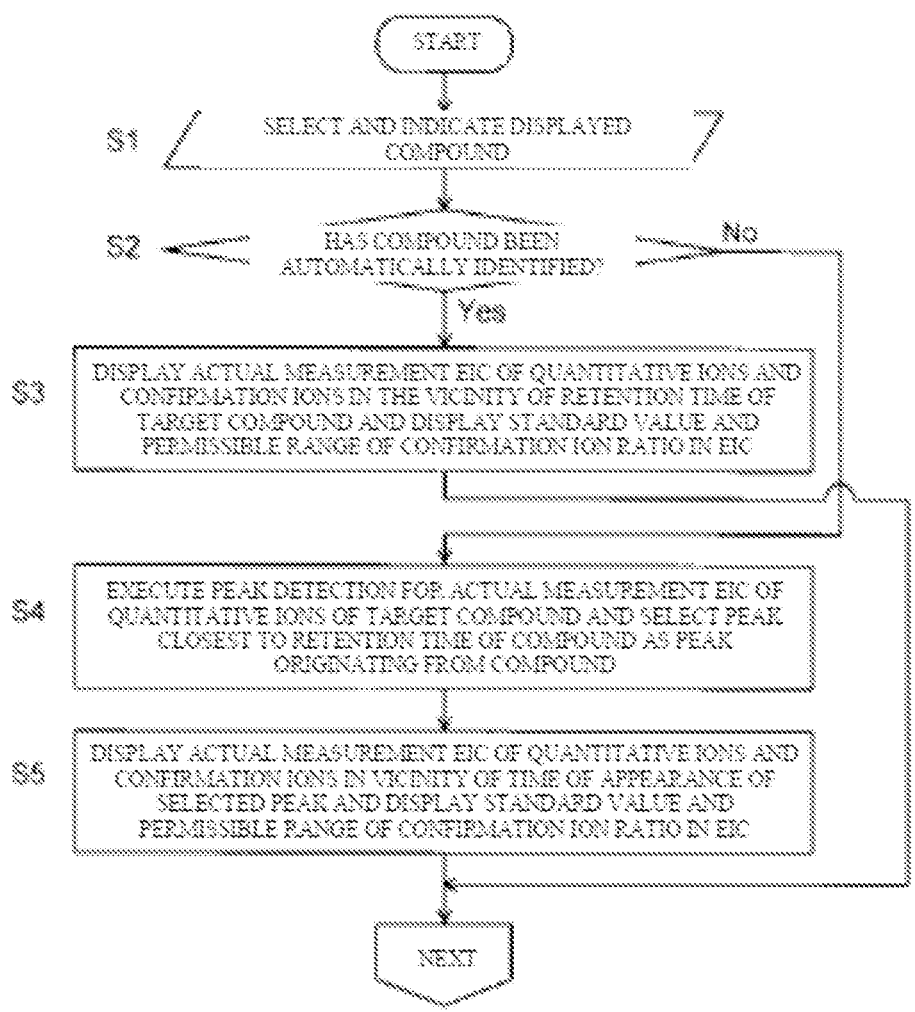
FIG. 3 is a flowchart showing an example of the procedure of the confirmation operation for identifying components in the GC-MS system of this embodiment.
Figure 4:
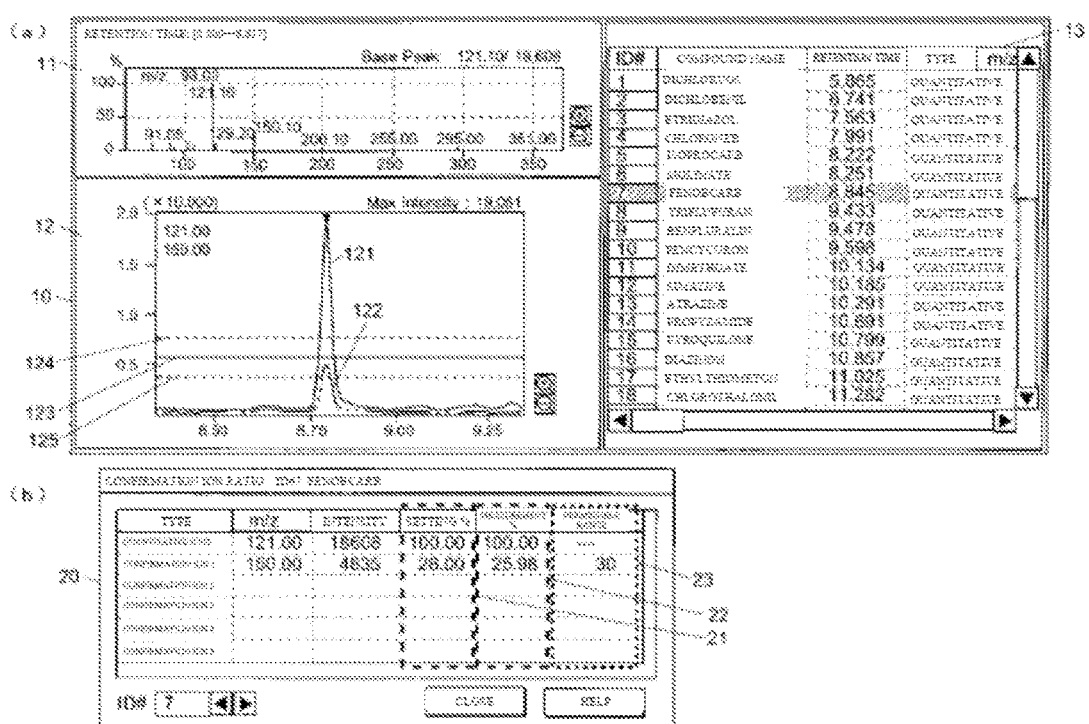
FIG. 4 is a schematic diagram showing an example of the display screen in the GC-MS system of this embodiment.

Next, data processing characteristic to the GC-MS system of this embodiment—more specifically, data processing for supporting the confirmation operation performed by the analyst when identifying components—will be described in accordance with the flowchart shown in FIG. 3. FIG. 4 is a schematic diagram showing an example of the screen displayed on the display part 8 at the time of this processing.

FIG. 4 (a) shows a data reanalysis screen 10, and FIG. 4 (b) shows a confirmation ion ratio screen 20. These may be arranged next to one another within the same screen, or the confirmation ion ratio screen 20 may be displayed so that it overlaps the data reanalysis screen 10. A mass spectrum display area 11, a chromatogram display area 12, and a compound table display area 13 are respectively marked out and arranged in the data reanalysis screen 10. The details of the graphs or tables displayed in each of the display areas will be described below.

When the analyst performs a prescribed operation with the operation part 7 in order to specify data to be analyzed, the data processing part 4 reads the measurement data stored in the measurement data saving part 5 as data to be processed. The data processing part 4 also extracts information regarding the compounds designated in a method file in which the analytical conditions used to obtain the measurement data that is read out are extracted from the standard data saving part 6, creates a compound table in which the compound names, retention times, and the like are listed, and displays this in the compound table display area 13 of the data reanalysis screen 10. The compounds registered in the compound table are compounds to be identified or compounds for which presence or absence is to be confirmed in this reanalysis.

Next, the data processing part 4 executes automatic identification processing for the measurement data that is read using the compound table. For example, an EIC for the mass-charge ratio of quantitative ions is created from the measurement data for each individual compound registered in the compound table, and peaks are detected within a prescribed permissible time range centered around the retention time defined for that compound in the EIC. The actual measurement mass spectrum at the time of the top peak out of these peaks is then compared to a standard mass spectrum defined for that compound, and if the degree of similarity calculated in accordance with a prescribed algorithm is equal to or greater than a threshold, it is determined that the peak in the EIC is a peak originating from the compound. On the other hand, if no peaks are detected within the prescribed permissible time range centered around the retention time in the EIC for the mass-charge ratio of the quantitative ions or if peaks are detected but the similarity of the mass spectra is low, it is assumed that the compound in question is not identified. In this way, automatic identification processing is executed for all of the compounds registered in the compound table to determine whether the compounds are identified or unidentified.

However, since automatic identification processing is ultimately performed mechanically in accordance with prescribed conditions, there is a possibility that misidentification or identification oversight may occur due to the deformation or distortion of peak waveforms as a result of the overlap of components or the influx of noise. Therefore, the analyst visually confirms the peak waveform shape and the peak heights of the EIC for the mass-charge ratio of the confirmation ions as described below and confirms whether the peaks used for identification are appropriate.

The analyst operates a mouse to select and indicate a compound to be confirmed in the compound table displayed in the compound table display area 13 of the data reanalysis screen 10 such as that shown in FIG. 4 (a) (step S1). In the example shown in FIG. 4 (a), "fenobcarb" of ID#:7 is designated, and this row of the compound table is highlighted as a result. The data processing part 4 receives the selection and indication of this compound and assesses whether the compound is a compound which has been automatically identified (step S2).

If the compound has been automatically identified, the data processing part 4 obtains information regarding the retention time and the mass-charge ratio of quantitative ions and confirmation ions for the designated compound and creates an EIC of quantitative ions and an EIC of confirmation ions based on the measurement data. EICs in a prescribed time range in the vicinity of the retention time of the compound in question are displayed in an overlapping manner within the boundaries of the same graph in the chromatogram display area 12. In FIG. 4 (a), an EIC of quantitative ions with a m/z of 121.00 is shown by symbol 121, and an EIC of confirmation ions with a m/z of 150.00 is shown by symbol 122. In this drawing, the line types of both EICs are varied, but the line colors should actually be varied so that the two can be distinguished. The data processing part 4 also creates an actual measurement mass spectrum at the time of the top peak of the EIC of quantitative ions based on the measurement data and displays it in the mass spectrum display area 11.

In addition, the data processing part 4 finds respective intensities from the peak areas at the retention times appearing in the EIC of quantitative ions and the EIC of confirmation ions based on actual measurements and calculates the actual confirmation ion ratio by calculating the intensity of confirmation ions while defining the intensity of quantitative ions as 100%. A confirmation ion ratio table for the designated compound shown in FIG. 4 (b) is then created based on the intensity values and confirmation ion ratios of actual measurements and information such as the standard values of confirmation ion ratios stored in the standard data saving part 6 (or registered in the compound table), and this is displayed in the confirmation ion ratio screen 20. In the confirmation ion ratio table shown in FIG. 4 (*b*), the setting % shown by the symbol 21 is the standard value of a confirmation ion ratio, and the measurement % shown by the symbol 22 is the confirmation ion ratio of actual measurements. The permissible range shown by the symbol 23 is the range of confirmation ion intensities permitted around the standard value of the confirmation ion ratio.

The data processing part 4 graphically displays the standard values and the permissible ranges of the confirmation ion ratios displayed in the confirmation ion ratio table in the chromatogram display area 12. That is, a horizontal standard center line 123 is drawn at the intensity position of the standard value of the confirmation ion ratio (28% in this example) when the intensity of the top peak in the EIC of quantitative ions is defined as 100%. In addition, an upper limit line 124 and a lower limit line 125 showing the permissible range (30% in this example) around the standard value of the confirmation ion ratio are also drawn (step S3). The standard center line 123 is a line showing the standard value of the confirmation ion ratio, and since the upper limit line 124 and the lower limit line 125 show the permissible range of the intensity of confirmation ions, it is possible to determine whether the confirmation ion ratio of the actual measurement is appropriate based on the degree to which the height of the top peak of the EIC 122 of confirmation ions deviates from the standard center line 123 and whether the height falls within the range determined by the upper limit line 124 and the lower limit line 125.

In step S2, if it is assessed that the selected and indicated compound is not a compound that has been automatically identified, the data processing part 4 obtains the retention time of the designated compound and information regarding the mass-charge ratio of quantitative ions and confirmation ions and creates an EIC of quantitative ions and an EIC of confirmation ions based on the measurement data. Peak detection is then executed for the EIC of quantitative ions, and the peak closest to the retention time of the compound from among the detected peaks is considered a peak originating from the compound in question (step S4). EICs within a prescribed range centered around the time at which this peak appears are then displayed in an overlapping manner within the boundaries of the same graph in the chromatogram display area 12.

Specifically, a peak within a time range of the retention time of the compound $\pm\alpha$ is extracted from among the detected peaks, and if there are a plurality of peaks, the peak with the largest peak area or the peak with the largest peak top value should be considered to be a peak originating from the compound in question. At this time, if the time range of the EIC displayed in the chromatogram display area 12 is set to the time range of the retention time $\pm\alpha$, all of the extracted peaks will be displayed in the EIC.

All other processing is as described above, wherein a horizontal standard center line is drawn at the intensity position of the standard value of the confirmation ion ratio when the intensity of the top peak in the EIC of quantitative ions is defined as 100% in the overlapping display of the EIC of quantitative ions and the EIC of confirmation ions displayed in the chromatogram display area 12, and an upper limit line and a lower limit line showing the permissible range centered around the standard value of the confirmation ion ratio are also drawn (step S5). As a result, even for a compound that has not been automatically identified, it is possible to confirm the most likely peak in the EIC based on the waveform shape or the confirmation ion ratio.

In addition, when the same confirmation is to be made with regard to other compounds differing from the compound previously designated in the compound table, the other compounds should be designated in the compound table. As described above, with the GC-MS system of this embodiment, the analyst can confirm whether a peak in the EIC used for the identification of a target compound is appropriate in light of the ideal confirmation ion ratio using simple operations at the time of the component identification operation based on measurement data collected previously.

In the embodiment described above, there was only one type of confirmation ion, but if there are a plurality of types of confirmation ions, actual measurement EICs should be displayed for all or some of the ions, and the standard values or permissible ranges of the confirmation ion ratios of the confirmation ions of the displayed EICs should be displayed in an overlapping manner in the EICs. If there are a plurality of confirmation ions, the colors of the lines showing the EICs or the standard values of the confirmation ion ratios should be made to differ for each confirmation ion.

Moreover, the embodiment described above is merely an example of the present invention, and it is clear that appropriate variations, modifications, or additions made within a scope adhering to the gist of the present invention are also included in the scope of the patent claims of this application.

EXPLANATION OF SYMBOLS

1 . . . gas chromatograph (GC)
2 . . . mass spectrometer (MS)
3 . . . personal computer (PC)
4 . . . data processing part
5 . . . measurement data saving part
6 . . . standard data saving part
7 . . . operation part
8 . . . display part
10 . . . data reanalysis screen
11 . . . mass spectrum display area
12 . . . chromatogram display area
13 . . . compound table display area
20 . . . confirmation ion ratio screen

What is claimed is:

1. A chromatograph mass spectrometry data processing device for creating extracted ion chromatograms with respect to specific mass-charge ratios based on data repeatedly collected over time by chromatograph mass spectrometry and displaying the chromatograms on a display screen, said device being provided with:

the display screen;

a memory which stores the retention times, the mass-charge ratios of quantitative ions characterizing each compound of a plurality of compounds and confirmation ions characterizing each compound and having a different mass-charge ratio from the quantitative ions, and standard values of a confirmation ion ratio expressing the ratio of the intensity of confirmation ions to quantitative ions for each of the compounds in advance;

a chromatogram display processor which creates extracted ion chromatograms of the quantitative ions and confirmation ions of target components designated to be confirmed in collected measurement data among the compounds stored in said memory and displays the chromatograms in an overlapping manner within the boundaries of the same graph; and an additional display processor which displays information showing the standard values of the confirmation ion ratio of the target compounds on the displayed extracted ion chromatograms graphically, wherein the standard values are obtained from said memory;

wherein the quantitative ions and the confirmation ions representing the confirmation ion ratio for one compound of the plurality of compounds are formed by ionization from the one compound of the plurality of compounds, both the quantitative ions and the confirmation ions characterizing the same compound, and wherein said additional display processor graphically displays information showing a permissible intensity range around the standard values of the confirmation ion ratios on the displayed extracted ion chromatograms.

2. The chromatograph mass spectrometry data processing device according to claim 1, wherein the information showing the standard values of the confirmation ion ratio of the target compounds comprises a standard center line.

3. The chromatograph mass spectrometry data processing device according to claim 1, wherein the additional display processor displays a numerical value of the confirmation ion ratio for the one compound of the plurality of compounds, and displays a numerical value of the standard values of the confirmation ion ratio of the target compounds.

4. A method of performing chromatograph mass spectrometry data processing for creating extracted ion chromatograms with respect to specific mass-charge ratios based on data repeatedly collected over time by chromatograph mass spectrometry and displaying the chromatograms on a display screen, the method comprising:

a) storing in a memory the retention times, the mass-charge ratios of quantitative ions characterizing each compound of a plurality of compounds and confirmation ions characterizing each compound and having a different mass-charge ratio from the quantitative ions, and standard values of a confirmation ion ratio expressing the ratio of the intensity of confirmation ions to quantitative ions for each of the compounds in advance;

b) creating extracted ion chromatograms of the quantitative ions and confirmation ions of target components designated to be confirmed in collected measurement data among the compounds stored in said memory and displaying the chromatograms in an overlapping manner within the boundaries of the same graph; and c) displaying information showing the standard values of the confirmation ion ratio of the target compounds on the displayed extracted ion chromatograms graphically, wherein the standard values are obtained from said memory;

wherein the quantitative ions and the confirmation ions representing the confirmation ion ratio for one compound of the plurality of compounds are formed by ionization from the one compound of the plurality of compounds, both the quantitative ions and the confirmation ions characterizing the same compound, and wherein the information showing the standard values of the confirmation ion ratio of the target compounds comprises a permissible intensity range around the standard values displayed on the displayed extracted ion chromatograms.

5. The method of claim 4, wherein the information showing the standard values of the confirmation ion ratio of the target compounds comprises a standard center line.

6. The method of claim 4, wherein a numerical value of the confirmation ion ratio for the one compound of the plurality of compounds is displayed, and a numerical value of the standard values of the confirmation ion ratio of the target compounds is displayed.

* * * * *